United States Patent [19]
Ito

[11] Patent Number: 5,291,403
[45] Date of Patent: Mar. 1, 1994

[54] METHOD OF AND APPARATUS FOR PROCESSING RADIATION IMAGE

[75] Inventor: Wataru Ito, Kanagawa, Japan

[73] Assignee: Fuji Photo Film Co., Ltd., Kanagawa, Japan

[21] Appl. No.: 779,311

[22] Filed: Oct. 18, 1991

[30] Foreign Application Priority Data

Oct. 19, 1990 [JP] Japan ................... 2-82806

[51] Int. Cl.$^5$ ............................................. G06F 15/00
[52] U.S. Cl. ................................ 364/413.23; 250/587; 378/62
[58] Field of Search .................. 364/413.23; 250/587; 358/111; 378/62

[56] References Cited

U.S. PATENT DOCUMENTS

| | | | |
|---|---|---|---|
| 4,258,264 | 3/1981 | Kotera et al. | 250/585 |
| 4,276,473 | 6/1981 | Kato et al. | 250/587 |
| 4,315,318 | 2/1982 | Kato et al. | 382/6 |
| 4,387,428 | 6/1983 | Ishida et al. | 364/413.13 |
| 4,710,875 | 12/1987 | Nakajima et al. | 364/413.13 |
| 4,816,681 | 3/1989 | Shimura | 250/327.2 |
| 5,049,746 | 9/1991 | Ito | 250/327.2 |
| 5,049,748 | 9/1991 | Ito et al. | 250/327.2 |
| 5,051,589 | 9/1991 | Arakawa | 250/327.2 |
| 5,051,902 | 9/1991 | Hishinuma | 364/413.13 |
| 5,210,415 | 5/1990 | Ito | 250/327.2 |
| 5,237,176 | 8/1993 | Ito | 250/587 |

FOREIGN PATENT DOCUMENTS

| | | |
|---|---|---|
| 56-11395 | 2/1981 | Japan . |
| 61-5193 | 2/1986 | Japan . |
| 64-23676 | 1/1989 | Japan . |
| 294563 | 2/1990 | Japan . |

Primary Examiner—Roy N. Envall, Jr.
Assistant Examiner—Laura Brutman
Attorney, Agent, or Firm—Sughrue, Mion, Zinn, Macpeak & Seas

[57] ABSTRACT

A plurality of original image signals which represent a plurality of radiation images are obtained by exposing recording media to radiations with different energy levels which have passed through an object constituted of a plurality of tissues exhibiting different levels of radiation absorptivity with respect to radiations with different energy levels. An extracted image signal representing an extracted image of a predetermined tissue in the object is obtained on the basis of the original image signals. A processed image signal representing a processed image is obtained by calculating a processed image signal component S' corresponding to a predetermined picture element in the extracted image according to formula $S' = S_{org} + \beta \cdot (S - S_{us})$ wherein Sus represents an unsharp mask signal obtained by averaging the extracted image signal components corresponding to a number of picture elements which surrounds a predetermined picture element within a predetermined region, Sorg represents the original image signal component corresponding to the predetermined picture element, S represents the extracted image signal corresponding to said predetermined picture element, and $\beta$ represents a coefficient, and by repeating the calculation according to the formula with all the picture elements in the extracted image being sequentially taken as the predetermined picture element.

10 Claims, 11 Drawing Sheets

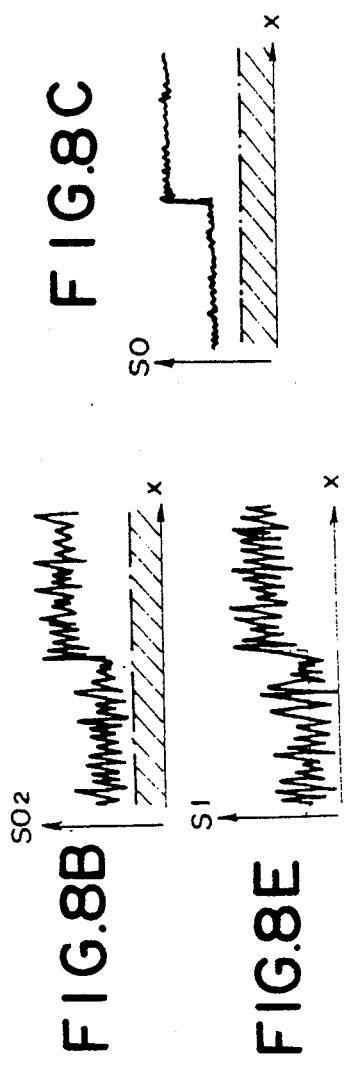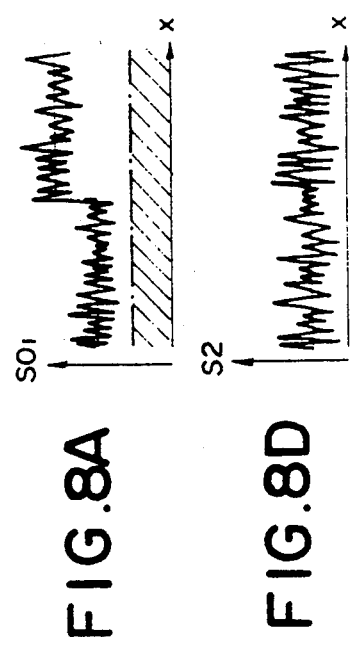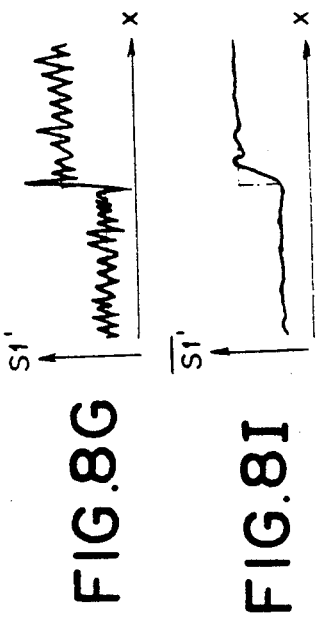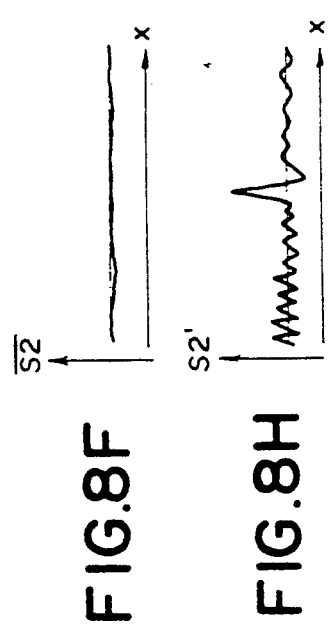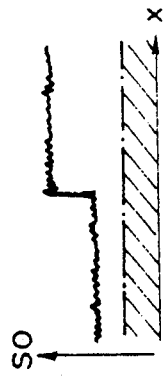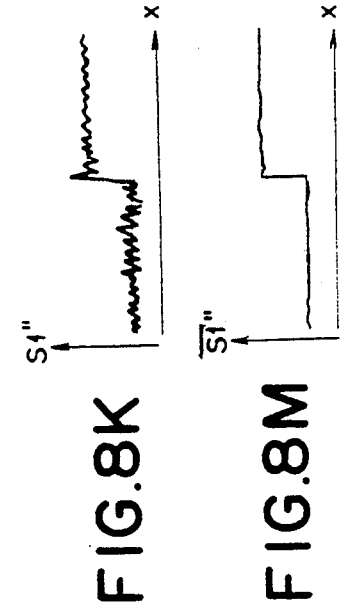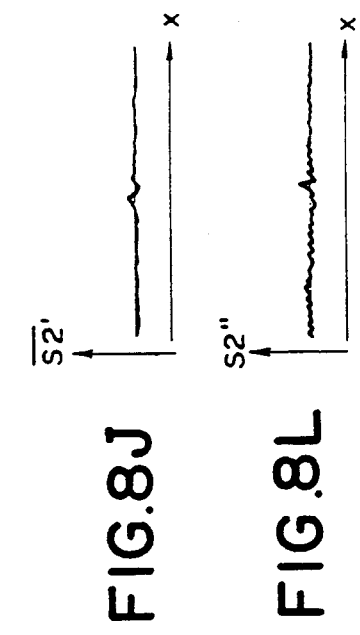

METHOD OF AND APPARATUS FOR PROCESSING RADIATION IMAGE

BACKGROUND OF THE INVENTION

1. Field of the Invention

This invention relates to processing of a radiation image signal and more particularly to a method of and apparatus for processing a radiation image in which frequency response processing can be selectively applied to only a pattern of a tissue out of patterns of a plurality of tissues falling within similar spatial frequency regions.

2. Description of the Prior Art

Techniques for reading out a recorded radiation image in order to obtain an image signal, carrying out appropriate image processing on the image signal, and then reproducing a visible image by use of the processed image signal have heretofore been known in various fields. For example, as disclosed in Japanese Patent Publication No. 61(1986)-5193, an X-ray image is recorded on an X-ray film having a small gamma value chosen according to the type of image processing to be carried out, the X-ray image is read out from the X-ray film and converted into an electric signal, and the electric signal (image signal) is processed and then used for reproducing the X-ray image as a visible image on a copy photograph or the like. In this manner, a visible image having good image quality with high contrast, high sharpness, high graininess, or the like can be reproduced.

When certain kinds of phosphors are exposed to radiation such as X-rays, $\alpha$-rays, $\beta$-rays, $\gamma$-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored thereon during its exposure to the radiation. A phosphor exhibiting such properties is referred to as a stimulable phosphor. As disclosed in U.S. Pat. Nos. 4,258,264, 4,276,473, 4,315,318, 4,387,428, and Japanese Unexamined Patent Publication No. 56(1981)-11395, it has been proposed to use stimulable phosphors in radiation image recording and reproducing systems. Specifically, a sheet provided with a layer of the stimulable phosphor (hereinafter referred to as a stimulable phosphor sheet) is first exposed to radiation which has passed through an object, such as the human body. In this manner, a radiation image of the object is stored on the stimulable phosphor sheet. The stimulable phosphor sheet, on which the radiation image has been stored, is then scanned with stimulating rays, such as a laser beam, which cause it to emit light in proportion to the amount of energy stored during exposure to the radiation. The light emitted by the stimulable phosphor sheet, upon stimulation thereof, is photoelectrically detected and converted into an electric image signal. The image signal is then used during the reproduction of the radiation image of the object as a visible image on a recording material such as photographic film, on a display device such as a cathode ray tube (CRT), or the like.

Radiation image recording and reproducing systems which use stimulable phosphor sheets are advantageous over conventional radiography using silver halide photographic materials, in that images can be recorded even when the energy intensity of the radiation to which the stimulable phosphor sheet is exposed varies over a wide range. More specifically, since the amount of light which the stimulable phosphor sheet emits when being stimulated varies over a wide range and is proportional to the amount of energy stored thereon during its exposure to the radiation, it is possible to obtain an image having a desirable density regardless of the energy intensity of the radiation to which the stimulable phosphor sheet was exposed. In order for the desired image density to be obtained, an appropriate read-out gain is set when the emitted light is being detected and converted into an electric signal (image signal) to be used in the reproduction of a visible image on a recording material, such as photographic film, or on a display device, such as a CRT.

In the radiation image recording system using an X-ray film or the stimulable phosphor sheet, the dose of radiation to which the object is exposed should be as small as possible especially when the object is a human body. However as the dose of radiation reduces, the graininess of the image deteriorates due to influence of quantum noise and the reproduced image becomes rough.

In order to overcome such a problem, there have been proposed various methods of improving the graininess of the image on the basis of the image signal taking into account other image qualities such as the sharpness of the image. (See, for instance, Japanese Unexamined Patent Publication No. 64(1989)-23676 and U.S. Pat. No. 5,051,902. In these methods, a specific spatial frequency component of a radiation image is emphasized relative to the other components in order to improve the total image quality.

However, when a single radiation image contains therein patterns of a plurality of tissues whose spatial frequency components overlap each other, there is a case where the frequency response processing contributes to improvement in the image quality of the pattern of one of the tissues but adversely affects the image quality of other tissues. For example, when, in a radiation image of the chest of a human body which is constituted of soft tissues such as the lungs and the heart and bones such as the ribs, the pattern of the soft tissues is to be reproduced as a visible image, frequency response emphasizing processing for improving ease of diagnosis through the pattern of the soft tissues emphasizes both the patterns of the soft tissues and the bones, and in the visible image reproduced on the basis of the processed image signal, the pattern of the bones near the soft tissues is too conspicuous though the image quality of the pattern of the soft tissues itself is improved.

SUMMARY OF THE INVENTION

In view of the foregoing observations and description, the primary object of the present invention is to provide a method of processing a radiation image in which frequency response processing can be selectively applied to only a pattern of a desired tissue in a radiation image of an object having a plurality of tissues.

Another object of the present invention is to provide an apparatus for carrying out the method.

In accordance with an aspect of the present invention, there is provided a method of processing a radiation image comprising the steps of detecting a plurality of original image signals which represent a plurality of radiation images obtained by exposing recording media to radiations with different energy levels which have passed through an object constituted of a plurality of tissues exhibiting different levels of radiation absorptivity with respect to radiations with different energy levels, obtaining an extracted image signal representing an extracted image of a predetermined tissue in the object on the basis of said plurality of original image signals, obtaining a processed image signal representing a processed image by calculating a processed image signal component S' corresponding to a predetermined picture element in the extracted image according to formula $$S' = Sorg + \beta \cdot (S - Sus)$$

wherein Sus represents an unsharp mask signal obtained by averaging the extracted image signal components corresponding to a number of picture elements which surrounds a predetermined picture element within a predetermined region, Sorg represents the original image signal component corresponding to said predetermined picture element, S represents the extracted image signal corresponding to said predetermined picture element, and $\beta$ represents a coefficient, and by repeating the calculation according to said formula with all the picture elements in the extracted image being sequentially taken as said predetermined picture element, thereby obtaining processed image signal components for all the picture elements in the processed image.

In accordance with another aspect of the present invention, there is provided a radiation image processing apparatus comprising a subtraction processing means which detects a plurality of original image signals which represent a plurality of radiation images obtained by exposing recording media to radiations with different energy levels which have passed through an object constituted of a plurality of tissues exhibiting different levels of radiation absorptivity with respect to radiations with different energy levels, and obtains an extracted image signal representing an extracted image of a predetermined tissue in the object on the basis of said plurality of original image signals, and a frequency response processing means which obtains a processed image signal representing a processed image by calculating a processed image signal component S' corresponding to a predetermined picture element in the extracted image according to formula $$S' = Sorg + \beta \cdot (S - Sus)$$

wherein Sus represents an unsharp mask signal obtained by averaging the extracted image signal components corresponding to a number of picture elements which surrounds a predetermined picture element within a predetermined region, Sorg represents the original image signal component corresponding to said predetermined picture element, S represents the extracted image signal corresponding to said predetermined picture element, and $\beta$ represents a coefficient, and by repeating the calculation according to said formula with all the picture elements in the extracted image being sequentially taken as said predetermined picture element, thereby obtaining processed image signal components for all the picture elements in the processed image.

The coefficient $\beta$ may be a positive or negative constant or a variable disclosed in the Japanese unexamined patent publications described above.

In the present invention, the method of obtaining the extracted image from the original image need not be limited to a specific method, but it is preferred that a method which can sufficiently eliminate the noise components from the extracted image, e.g., the method disclosed in Japanese Unexamined Patent Publication No. 2(1990)-94563, be employed.

In accordance with the present invention, an extracted image signal representing a predetermined tissue of an object (e.g. the pattern of soft tissues) is obtained on the basis of a plurality of original image signals each representing an original image comprising, for instance, patterns of soft tissues and bones, and calculation is made according to formula $S' = Sorg + \beta \cdot (S - Sus)$. Accordingly, a processed original image in which the frequency response process has been selectively applied only to a desired tissue (e.g., soft tissue) can be obtained.

BRIEF DESCRIPTION OF THE DRAWINGS

FIGS. 8A through 8M are graphs showing the profiles of the images, shown in FIG. 7, along a predetermined direction.

DESCRIPTION OF THE PREFERRED EMBODIMENTS

The present invention will hereinbelow be described in further detail with reference to the accompanying drawings. In the embodiments described below, X-ray images are stored on stimulable phosphor sheets.

Figure 9:
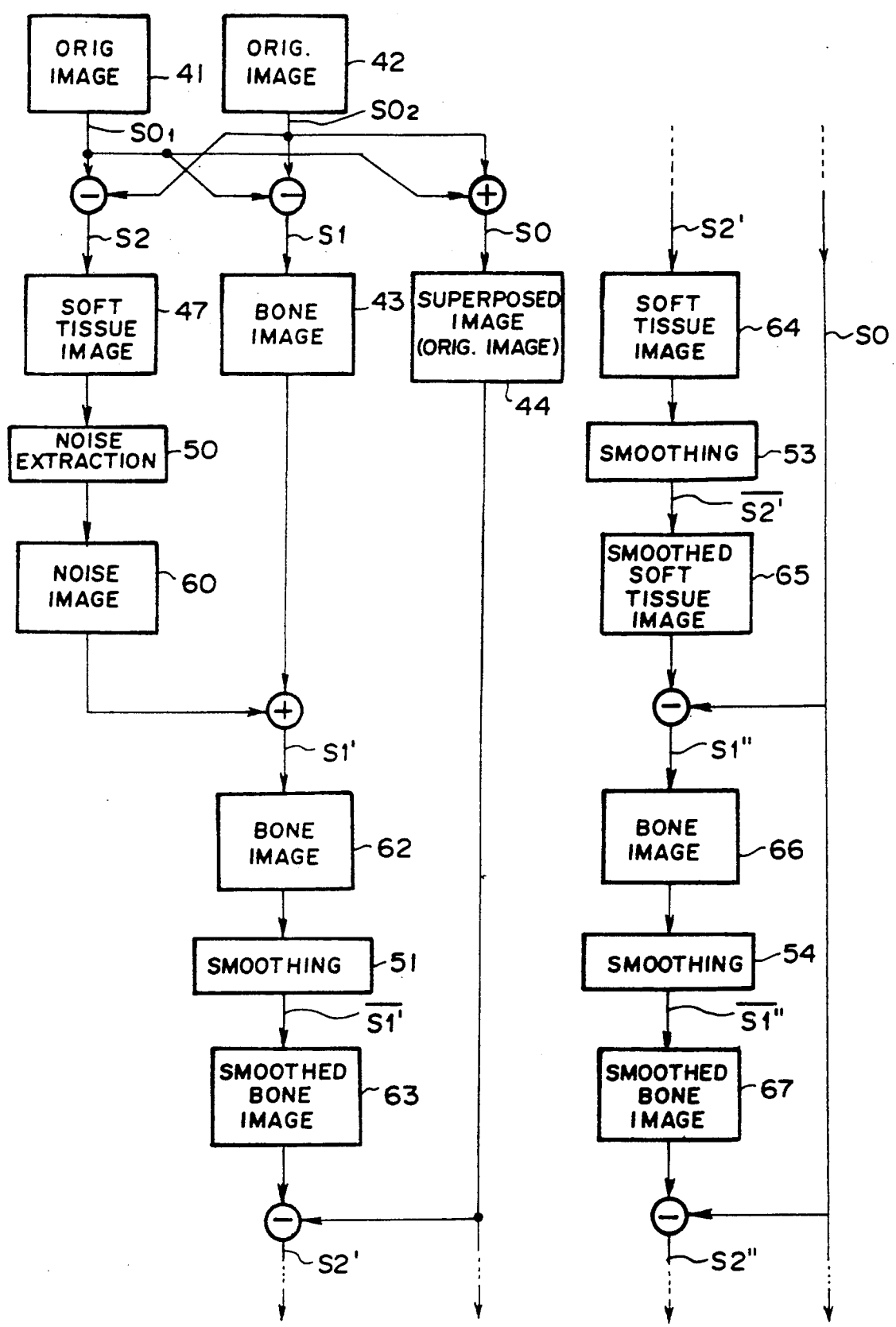
FIG. 9 is a flow chart showing processes substantially identical with those shown in FIG. 7.
Figure 12:
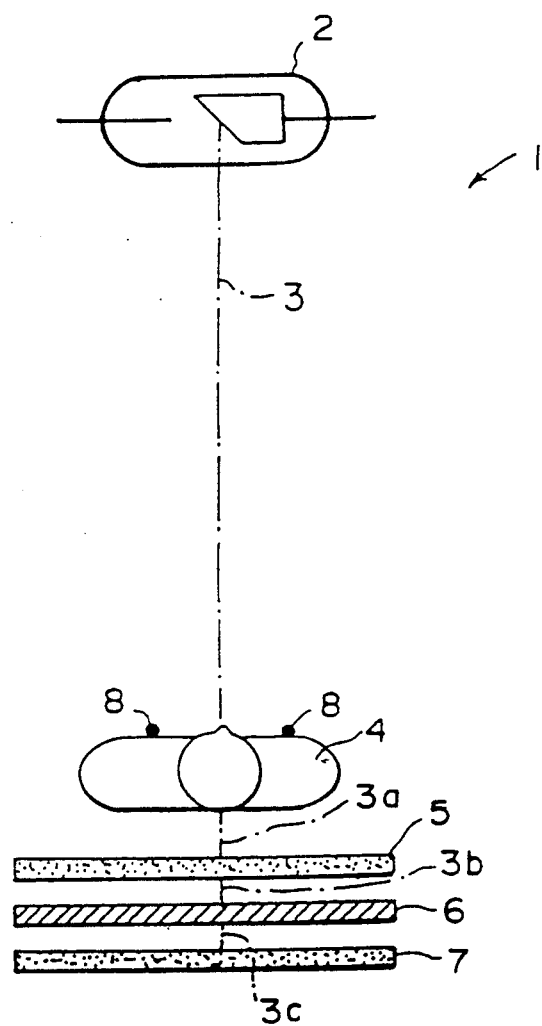
FIG. 12 is a schematic view showing an X-ray image recording apparatus.

FIG. 12 is a schematic view showing an X ray image recording apparatus 1. With reference to FIG. 9, X-rays 3 are produced by an X-ray tube 2 of the X-ray image recording apparatus 1 and irradiated to an object 4 (in this example, the chest of a human body). X-rays 3a, which have passed through the object 4, impinge upon a first stimulable phosphor sheet 5, and the comparatively low energy components of the X-rays 3a are stored on the first stimulable phosphor sheet 5. In this manner, an X-ray image of the object 4 is stored on the first stimulable phosphor sheet 5. X-rays 3b, which have passed through the first stimulable phosphor sheet 5, then pass through a filter 6 for filtering out the low energy components of the X-rays. X-rays 3c, which have passed through the filter 6 and are composed of the high energy components, impinge upon a second stimulable phosphor sheet 7. In this manner, an X-ray image of the object 4 is stored on the second stimulable phosphor sheet 7. During the image recording operation, a pair of marks 8 are placed on the object 4. The images of the marks 8 are utilized in the course of adjusting the positions of the two X-ray images so that the two X-ray images coincide with each other.

In the X-ray image recording apparatus 1, the X-ray images are stored on the first stimulable phosphor sheet 5 and the second stimulable phosphor sheet 7 with a single recording operation. Alternatively, the two X-ray images may be recorded one after the other with two independent recording operations.

Figure 13:
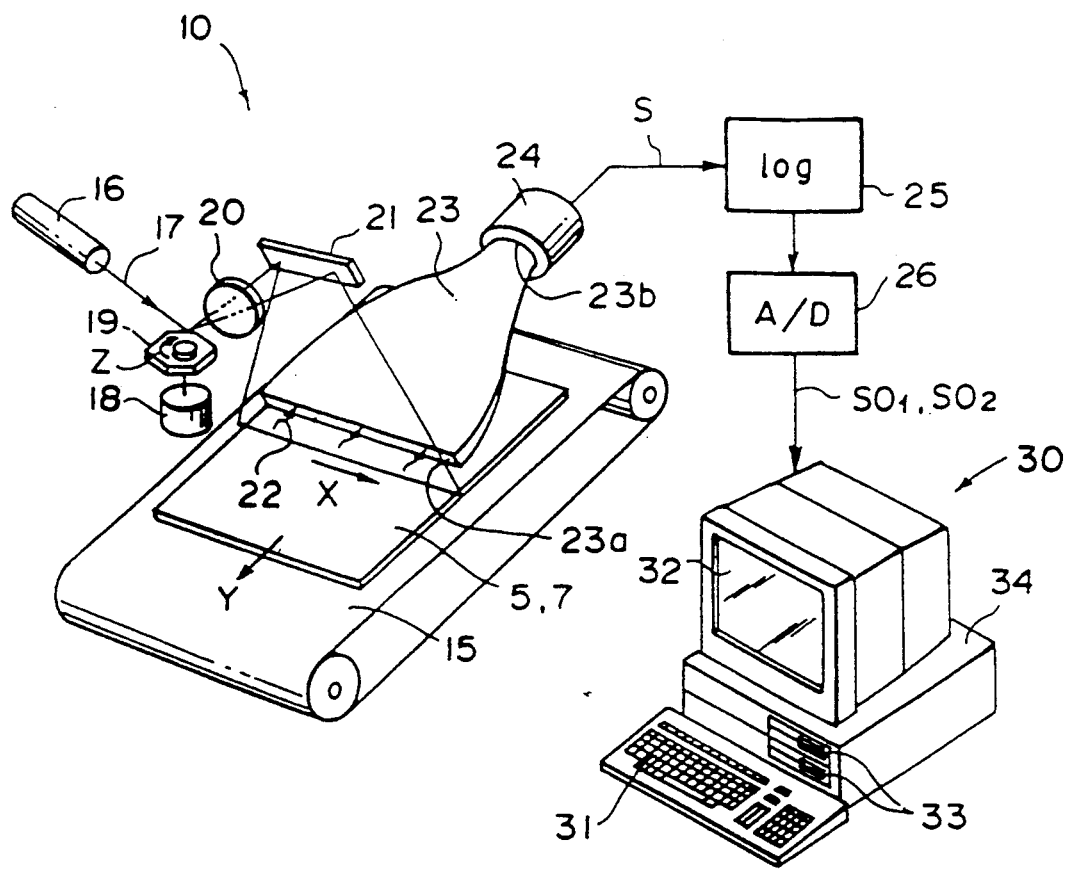
FIG. 13 is a perspective view showing an X-ray image read-out apparatus and an image processing and displaying apparatus wherein an embodiment of the method for forming an energy subtraction image in accordance with the present invention is employed.

FIG. 13 is a perspective view showing an X-ray image read-out apparatus 10 and an image processing and displaying apparatus 30 wherein an embodiment of the method for forming an energy subtraction image in accordance with the present invention is employed.

After the first X-ray image and the second X-ray image have been stored respectively on the first stimulable phosphor sheet 5 and the second stimulable phosphor sheet 7 in the X-ray image recording apparatus 1 shown in FIG. 12, the first stimulable phosphor sheet 5 and the second stimulable phosphor sheet 7 are placed one after the other at a predetermined position in the X-ray image read-out apparatus 10 shown in FIG. 13. How the first X-ray image is read out from the first stimulable phosphor sheet 5 will be described hereinbelow.

With reference to FIG. 13, the first stimulable phosphor sheet 5 is conveyed in a sub-scanning direction indicated by the arrow Y by a sheet conveyance means 15, which is constituted of an endless belt or the like and which is operated by an operating means (not shown). A laser beam 17, which serves as stimulating rays, is produced by a laser beam source 16. The laser beam 17 is reflected and deflected by a rotating polygon mirror 19, which is being quickly rotated by a motor 18 in the direction indicated by the arrow Z. The laser beam 17 then passes through a converging lens 20, which is constituted of an fθ lens or the like. The direction of the optical path of the laser beam 17 is then changed by a mirror 21, and the laser beam 17 is caused to impinge upon the first stimulable phosphor sheet 5 and scan it in a main scanning direction indicated by the arrow X. The main scanning direction is approximately normal to the sub-scanning direction indicated by the arrow Y. When the first stimulable phosphor sheet 5 is exposed to the laser beam 17, the exposed portion of the first stimulable phosphor sheet 5 emits light 22 in an amount proportional to the amount of energy stored thereon during its exposure to the X-rays. The emitted light 22 is guided by a light guide member 23, and photoelectrically detected by a photomultiplier 24.

The light guide member 23 is made from a light guiding material, such as an acrylic plate. The light guide member 23 has a linear light input face 23a, positioned to extend along the main scanning line on the first stimulable phosphor sheet 5, and a ring-shaped light output face 23b, positioned so that it is in close contact with a light receiving face of the photomultiplier 24. The emitted light 22, which has entered the light guide member 23 from its light input face 23a, is guided through repeated total reflection inside of the light guide member 23, emanates from the light output face 23b, and is received by the photomultiplier 24. In this manner, the amount of the emitted light 22, which amount represents the first X-ray image stored on the first stimulable phosphor sheet 5, is converted into an electric signal by the photomultiplier 24.

An analog signal S generated by the photomultiplier 24 is logarithmically amplified by a logarithmic amplifier 25, and fed into an A/D converter 26. The A/D converter 26 samples the analog signal S, and the sampled signal is converted into a digital image signal SO. The image signal SO thus obtained represents the first X-ray image, which was stored on the first stimulable phosphor sheet 5, and will hereafter be referred to as the first image signal $SO_1$. The first image signal $SO_1$ is stored in an internal memory of the image processing and displaying apparatus 30.

The image processing and displaying apparatus 30 is provided with a keyboard 31, from which various instructions are entered, and a CRT display device 32, which displays auxiliary information for instructions and a visible image represented by an image signal. The image processing and displaying apparatus 30 is also provided with a floppy disk drive unit 33, which receives and operates a floppy disk serving as an auxiliary storage medium, and a main body 34 which incorporates a CPU and the internal memory.

Thereafter, in the same manner as that described above, a second image signal $SO_2$ is obtained which represents the second X-ray image stored on the second stimulable phosphor sheet 7. The second image signal $SO_2$ is stored in the internal memory of the image processing and displaying apparatus 30.

Figure 1:
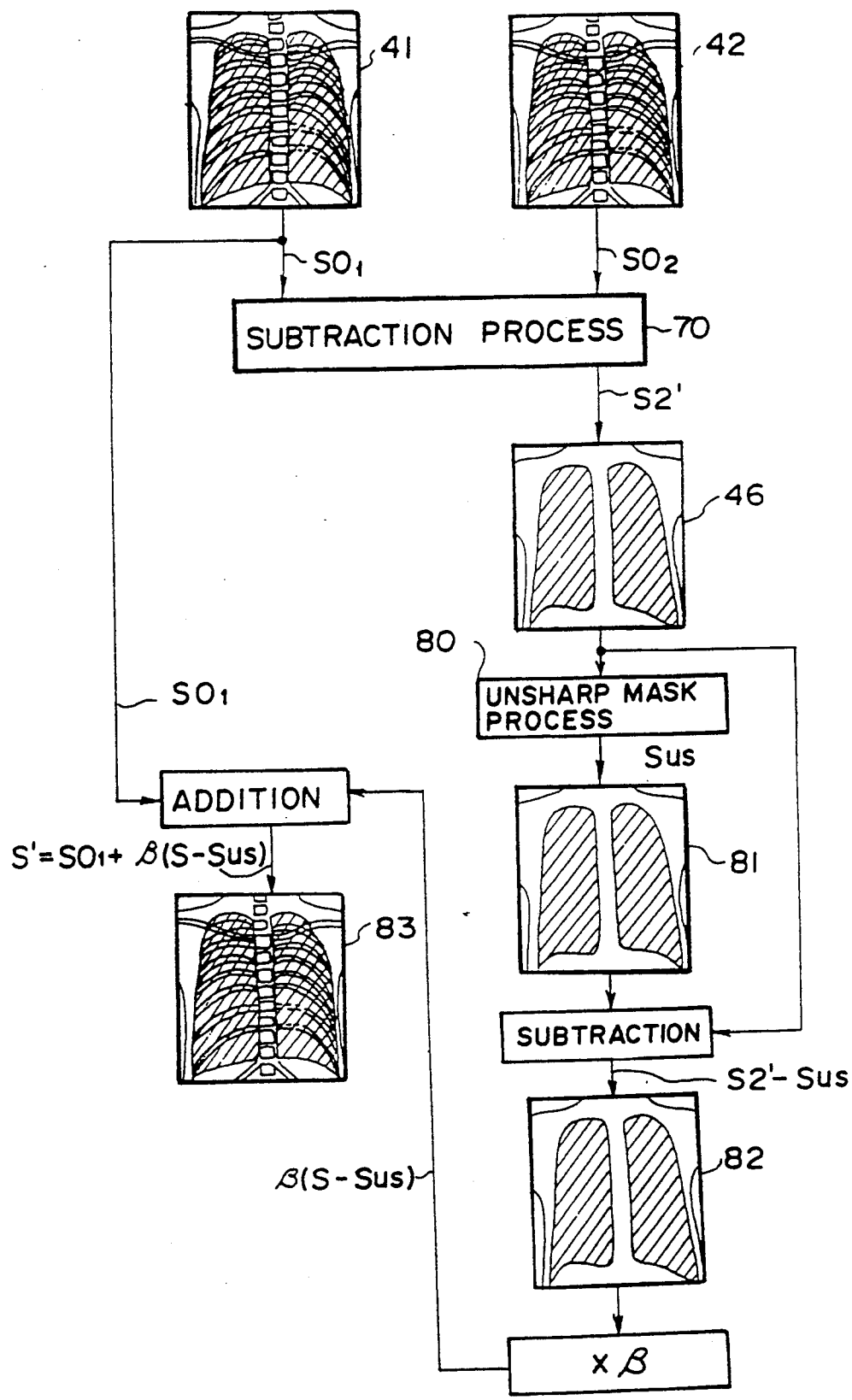
FIG. 1 is a flow chart showing the processes which are carried out in the image processing and displaying apparatus.

FIG. 1 is a flow chart showing the processes which are carried out in the image processing and displaying apparatus 30. The processes are carried out on basis of the first image signal $SO_1$ representing the first X-ray image and the second image signal $SO_2$ representing the second X-ray image, which signals are stored in the internal memory of the image processing and displaying apparatus 30.

The first image signal $SO_1$ and the second image Signal $SO_2$, which are stored in the internal memory of the image processing and displaying apparatus 30, represent a first X-ray image 41 and a second X-ray image 42 shown in FIG. 1. The first X-ray image 41 has been recorded with the comparatively low energy components of the X-rays. The second X-ray image 42 has been recorded with the comparatively high energy components of the X-rays. Both of the first X-ray image 41 and the second X-ray image 42 are original images composed of patterns of soft tissues and bones. The levels of image density of the soft tissue patterns and the bone patterns are different between the first X-ray image 41 and the second X-ray image 42.

The first image signal $SO_1$ and the second image signal $SO_2$ are read from the internal memory of the image processing and displaying apparatus 30. Position adjustment processing is then carried out on the first image signal $SO_1$ and the second image signal $SO_2$ such that the positions of the first X-ray image 41 represented by the first image signal $SO_1$ and the second X-ray image 42 represented by the second image signal $SO_2$ may coincide with each other. For this purpose, a method disclosed in, for example, U.S. Pat. No. 4,710,875 may be employed. With the position adjustment processing, one of the two X-ray images is linearly moved or rotated with respect to the other X-ray image until the images of the marks 8 in one X-ray image, which marks are shown in FIG. 12, overlap the images of the marks 8 in the other X-ray image. Thereafter, a subtraction process 70 is carried out on the basis of the first image signal $SO_1$ and the second image signal $SO_2$.

Figure 2:
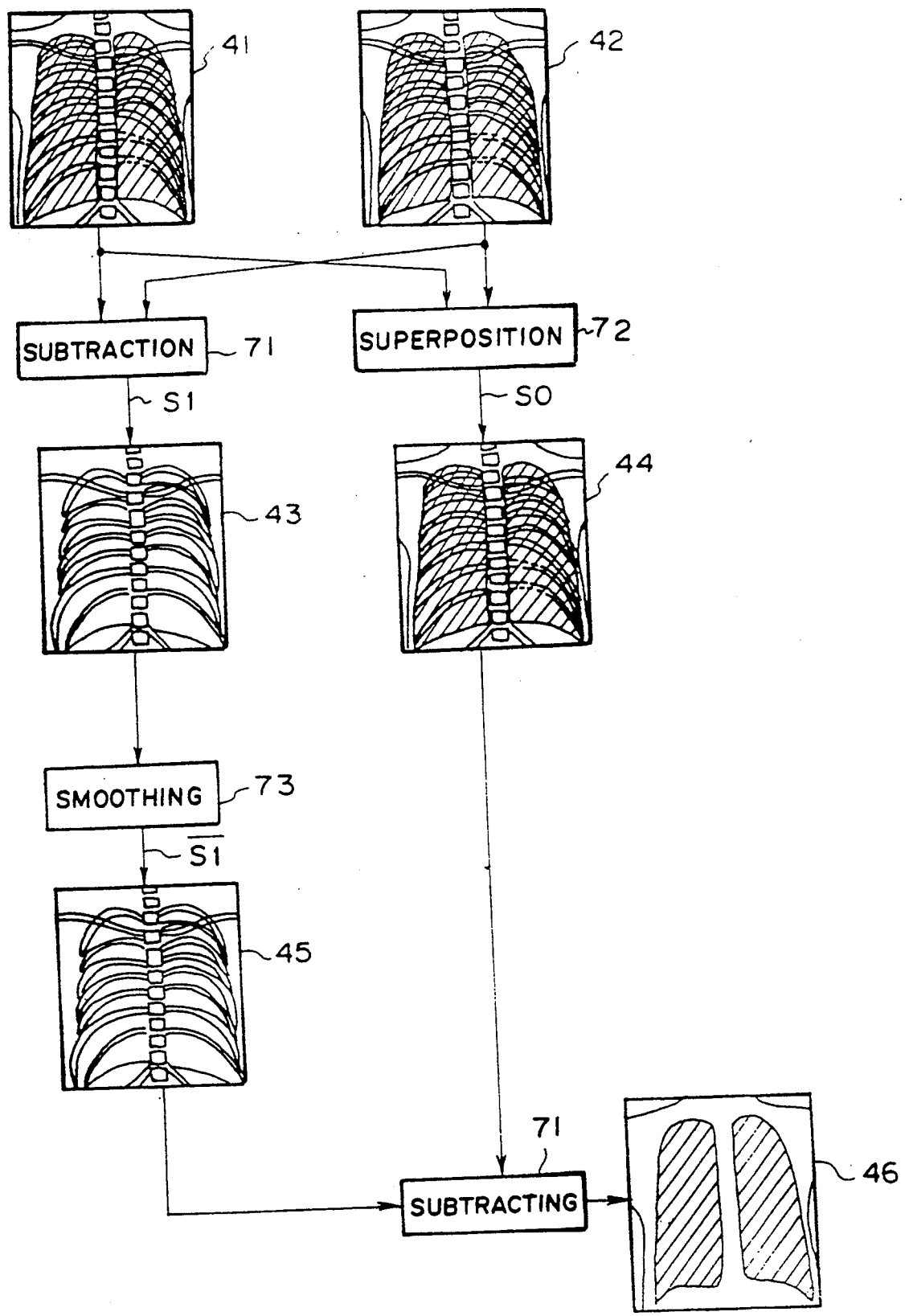
FIG. 2 is a flow chart showing an example of the subtraction process.

FIG. 2 is a flow chart showing an example of the subtraction process 70.

Specifically, X-ray absorption coefficients $\mu$ are classified into the following:

$\mu L^T$: Absorption coefficient of soft tissues with respect to the low energy components of X-rays.

$\mu H^T$: Absorption coefficient of soft tissues with respect to the high energy components of X-rays.

$\mu L^B$: Absorption coefficient of bones with respect to the low energy components of X-rays.

$\mu H^B$: Absorption coefficient of bones with respect to the high energy components of X-rays.

The first image signal $SO_1$ and the second image signal $SO_2$ are weighted, and the image signal components of the weighted image signals are subtracted from each other which represent the image information stored at corresponding picture elements in the two X-ray images. Thus a bone image signal S1 is obtained, which can be expressed as $$S1 = SO_1 - \frac{\mu L^T}{\mu H^T} SO_2 + C \tag{1}$$

where C denotes a bias component.

The bone image signal S1 represents a bone image 43 shown in FIG. 2, which image is composed of the bone patterns. The first image signal $SO_1$ and the second image signal $SO_2$ may be weighted in a different way, and the image signal components of the weighted image signals may be subtracted from each other which represent the image information stored at corresponding picture elements in the two X-ray images. Thus a soft tissue image signal S2 can be obtained, which is expressed as $$S2 = \frac{\mu L^B}{\mu H^B} SO_2 - SO_1 + C' \tag{2}$$

where C' denotes a bias component. The soft tissue image signal S2 represents a soft tissue image composed of the soft tissue patterns. However, in this embodiment, the operations for generating the soft tissue image signal S2 need not be carried out.

Also, the image signal components of the first image signal $SO_1$ and the second image signal $SO_2$ are added to each other which represent the image information stored at corresponding picture elements in the two X-ray images. Thus a superposition image signal SO is obtained, which can be expressed as $$SO = (SO_1 + SO_2)/2 \tag{3}$$

The superposition image signal SO represents a superposition image 44 shown in FIG. 2, which results from the superposition of the first X-ray image 41 and the second X-ray image 42 upon each other. The superposition image 44 can be referred to as an original image composed of the soft tissue patterns and the bone patterns. The first X-ray image 41 or the second X-ray image 42 may be utilized in lieu of the superposition image 44. However, the superposition image 44 should preferably be utilized. This is because the superposition image 44, which is obtained from the superposition of the first X-ray image 41 and the second X-ray image 42 upon each other, includes less noise components than the first X-ray image 41 and the second X-ray image 42, and therefore is advantageous for the subsequent processes.

Thereafter, the bone image signal S1 is processed such that noise components contained in the bone image 43 may be eliminated.

Figure 3:
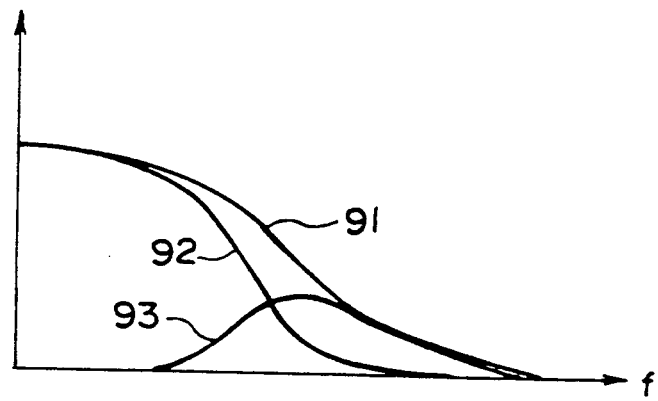
FIG. 3 is a graph showing spatial frequency spectra of a bone image and an image obtained by processing the bone image signal representing the bone image.

FIG. 3 is a graph showing spectra of a bone image and an image, which is obtained by processing the bone image signal representing the bone image, with respect to the spatial frequency, f.

In FIG. 3, curve 91 indicates the spectrum of the bone image 43, and curve 93 indicates the spectrum of noise components included in the bone image 43.

First, a smoothing process 73 (FIG. 2) is carried out on the bone image signal S1. As the smoothing process, one of various processes may be employed. For example, a simple averaging process may be employed wherein the mean value of the values of the image signal components of an image signal, which represent the picture elements belonging to a predetermined region having a predetermined picture element in the middle, is calculated and employed as the value of the image signal component representing the predetermined picture element. Alternatively, a median filter process may be employed wherein the median value of the values of the image signal components of an image signal, which represent the picture elements belonging to a predetermined region having a predetermined picture element in the middle, is calculated and employed as the value of the image signal component representing the predetermined picture element. As another alternative, an edge keeping filter (V-filter) process may be employed wherein a predetermined region having a predetermined picture element in the middle is divided into a plurality of small regions, and the variance of the values of the image signal components corresponding to each small region is calculated. A small region associated with the smallest variance is then found, and the mean value of the values of the image signal components corresponding to the small region associated with the smallest variance is employed as the value of the image signal component representing the predetermined picture element. As a further alternative, a process may be employed wherein Fourier transformation is carried out on an image signal, the signal obtained from the Fourier transformation is subjected to an operation for removing high spatial frequency components corresponding to noise components, and thereafter inverse Fourier transformation is carried out. However, the unsharp mask processing (the simple averaging process) has the drawbacks in that edges in the image become unsharp. The median filter process has the drawbacks in that, because picture elements are interchanged, contour line-like artifacts often occur. The edge keeping filter process has the drawbacks in that honeycomb-like artifacts often occur. The Fourier transformation process has the drawbacks in that a long time is taken for operations to be carried out. Therefore, in this embodiment, as will be described below, a smoothing process is carried out in which a filter adaptive to a probability density function is utilized. With the smoothing process, noise can be eliminated such that edges, which it is necessary to reproduce, may be kept sharp and no artifact may occur in the smoothed image. Also, noise can be eliminated quickly with simple operations.

Specifically, first, each of the picture elements in the bone image 43 is taken as a predetermined picture element, and the probability density function of the image signal components of the bone image signal S1 is generated, which represent a plurality of the picture elements belonging to a predetermined region having the predetermined picture element in the middle.

Figure 4A:
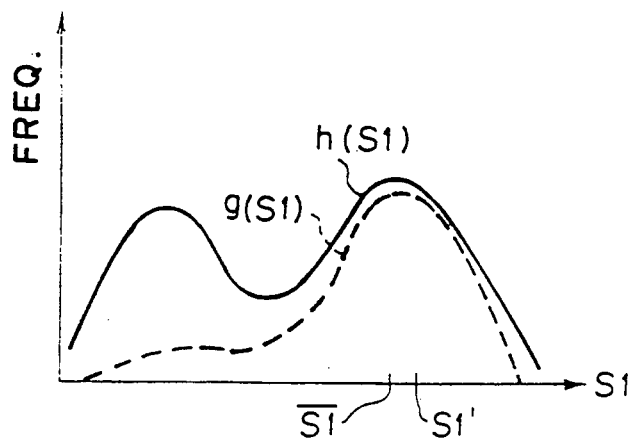
FIGS. 4A and 4B are graphs showing examples of probability density functions of image signal components, which image signal components represent a plurality of picture elements belonging to a predetermined region having a predetermined picture element in the middle.
Figure 4B:
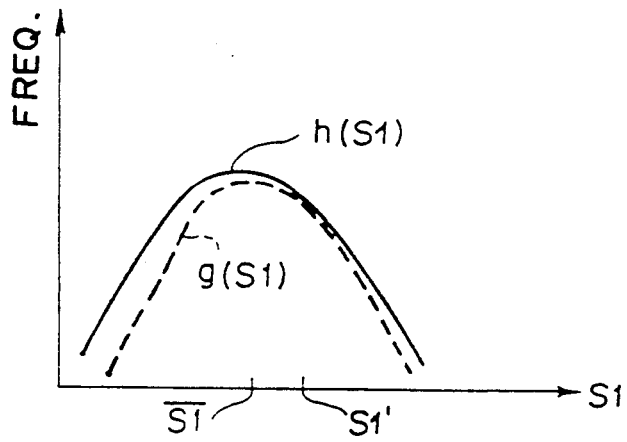

FIGS. 4A and 4B are graphs showing examples of probability density functions of image signal components of the image signal S1, which image signal components represent a plurality of picture elements belonging to a predetermined region having a predetermined picture element in the middle. The image signal component representing the predetermined picture element has a value S1'.

Figure 5:
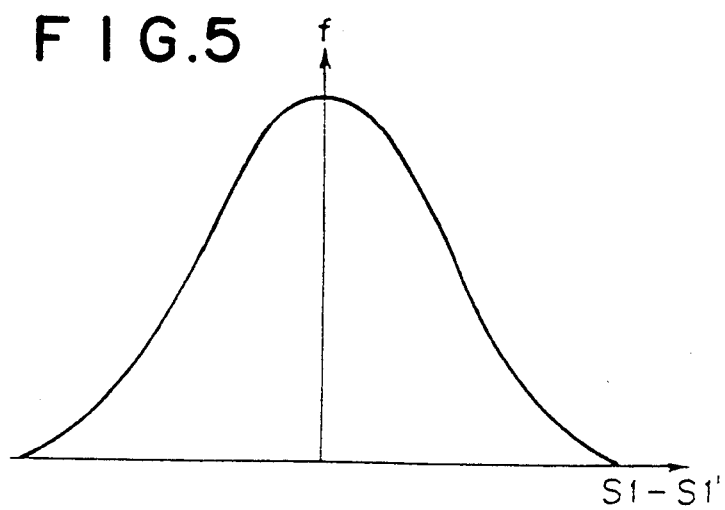
FIG. 5 is a graph showing an example of a function, in which the difference between the value of an image signal S1 and the value S1' of the image signal component representing a predetermined picture element located in the middle of a predetermined region serves as a variable.

FIG. 5 is a graph showing an example of a function, in which the difference between the value of the image signal S1 and the value S1' of the image signal component representing the predetermined picture element located in the middle of the predetermined region serves as a variable.

The probability density functions shown in FIGS. 4A and 4B are denoted by h(S1). Also, a function, the value of which decreases monotonously as the absolute value $|S1 - S1'|$ increases, e.g. the function shown in FIG. 5, is denoted by f(S1 − S1'). The values of a function g(S1) representing how frequently the values of image signal components of an image signal occur, which image signal has been processed, are calculated with the formula $$g(S1) = h(S1) \times f(S1 - S1') \quad (4)$$

In cases where the function h(S1) includes a plurality of peaks as shown in FIG. 4A, the function g(S1) has the effects of extracting only the peak, to which the image signal component having the value of S1' and representing the predetermined picture element belongs.

After the values of the function g(S1) have been calculated with Formula (4), the values of the image signal components of the image signal S1, which image signal components represent the picture elements belonging to the predetermined region, are weighted with the values of the function g(S1). A calculation is then made to find a mean-level value $\overline{S1}$ the weighted values of the image signal components of the image signal S1. Specifically, by way of example, the moment of first order of the function g(S1) is calculated with the formula $$\overline{S1} = \eta g(S1) \times S1 dS1 / \int S1 dS1 \quad (5)$$

The picture elements in the bone image 43 are sequentially taken as the predetermined picture element, and the processes with Formulas (4) and (5) are carried out for all of the picture elements in the bone image 43. In this manner, a smoothed image signal $\overline{S1}$ is generated. (As an aid in facilitating the explanation, the same reference numeral is utilized to indicate both the value of the image signal component representing each picture element and the image signal representing the whole image.) As indicated by curve 92 in FIG. 3, the smoothed image signal $\overline{S1}$ is generated by primarily eliminating the high spatial frequency components from the bone image signal S1. As shown in FIG. 4A, as for a picture element located in the vicinity of an edge, the smoothed image signal has $\overline{S1}$ the mean-level value of the values belonging only to the peak, to which said picture element belongs. Therefore, edges in the bone image 43 can be kept sharp.

Thereafter, the superposition image signal SO, which is expressed as Formula (3) and represents the superposition image 44, and the smoothed image signal $\overline{S1}$ are weighted. The image signal components of the weighted smoothed image signal $\overline{S1}$ are subtracted from the image signal components of the weighted superposition image signal SO, which image signal components represent the image information stored at corresponding picture elements in the two X-ray images. (subtraction 71) Thus a soft tissue image signal S2' is obtained, which can be expressed as $$S2' = SO - \frac{\left(1 + \frac{\mu_L^B}{\mu_H^B}\right)}{2 \cdot \left(\frac{\mu_L^B}{\mu_H^B} - \frac{\mu_L^T}{\mu_H^T}\right)} S1 + C' \quad (6)$$

where C'' denotes a bias component. The soft tissue image signal S2' represents a processed soft tissue image 46 shown in FIG. 2. The processed soft tissue image 46 has approximately the same image information as the soft tissue image expressed as Formula (2) and includes less noise components than the soft tissue image expressed as Formula (2). An unsharp mask process (to be described later) is carried out on the soft tissue image signal S2' thus obtained as shown in FIG. 1.

In the embodiment described above, the soft tissue image signal S2' is generated by smoothing the bone image signal S1 and subtracting the smoothed signal from the original image signal representing the original image. In cases where a bone image is to be reproduced., the soft tissue image signal S2 is generated with Formula (2) and then smoothed. The smoothed signal is then subtracted from the original image signal representing the original image. In this manner, a bone image in which noise components have been reduced can be obtained.

Another method for forming an energy subtraction image which is substantially identical with the method described above in conjunction with FIG. 2 will be described hereinbelow.

Figure 6:
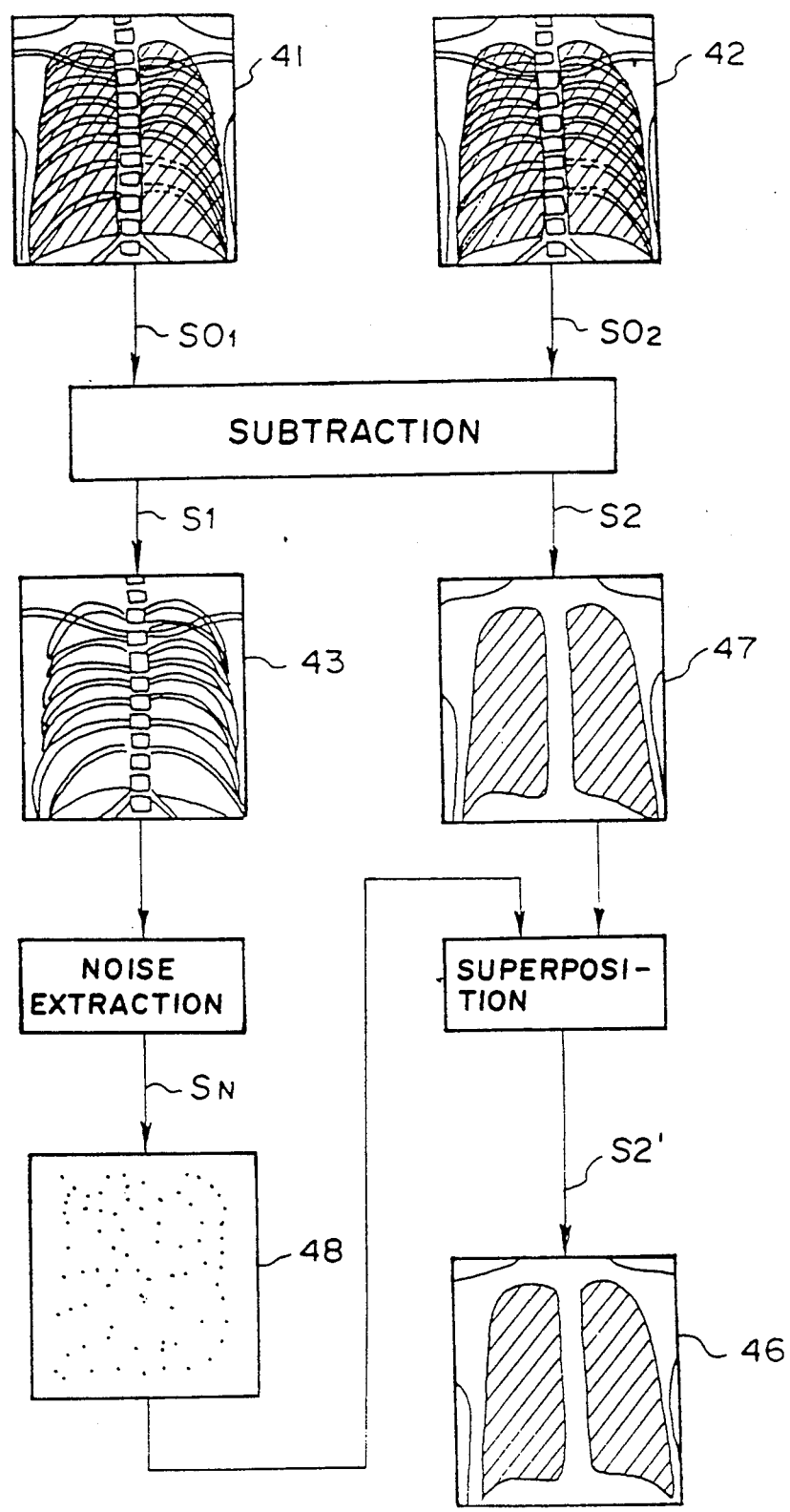
FIG. 6 is a flow chart showing another subtraction process which is substantially identical with that shown in FIG. 2 and is carried out in the image processing and displaying apparatus.

As an aid in explaining the method, FIG. 6 shows how the image processing and displaying apparatus 30 carries out the processes on the first image signal $SO_1$ representing the first X-ray image and the second image signal $SO_2$ representing the second X-ray image, which signals are stored in the internal memory of the image processing and displaying apparatus 30. In FIG. 6, similar elements are numbered with the same reference numerals with respect to FIG. 2.

First the bone image signal S1 and the soft tissue image signal S2 are obtained according to Formulae (1) and (2).

Thereafter, in the same manner as that described above in conjunction with FIG. 2, the smoothed image signal $\overline{S1}$ representing the smoothed bone image, in which the noise components included in the bone image 43 have been reduced, is generated by processing the bone image signal S1 in accordance with Formulas (4) and (5). The image signal components of the smoothed image signal $\overline{S1}$ are then subtracted from the image signal components of the bone image signal S1, which image signal components represent the image information stored at corresponding picture elements in the two X-ray images. Thus a noise signal SN representing a noise image 48, which is composed of only the noise components, is obtained. The noise signal SN can be expressed as $$SN = S1 - \overline{S1} \qquad (8)$$

As indicated by curve 93 in FIG. 4, the noise signal SN is composed of only the noise components included in the bone image 43. In the smoothed image signal $\overline{S1}$ even if the information representing the edges in the bone image 43 has a level of spatial frequency as high as that of the noise components, the information representing the edges will not be lost. Therefore, by carrying out the calculations with Formula (7) to find the difference between the bone image signal S1 and the smoothed image signal $\overline{S1}$, the noise signal SN can be obtained in which the information representing the edges has been completely canceled. Accordingly, the noise signal SN more accurately represents only the noise components of the bone image 43 than when a smoothing process was carried out such that the information representing the edges may be lost.

Thereafter, the noise signal SN and the soft tissue image signal S2 representing the soft tissue image 47 shown in FIG. 6 are weighted, and the image signal components of the weighted image signals are added to each other, which image signal components represent the image information stored at corresponding picture elements in the two images. Thus a soft tissue image signal S2′ is obtained, which represents a processed soft tissue image 46 shown in FIG. 6. The processed soft tissue image 46 has approximately the same image information as the soft tissue image 47 and includes less noise components than the soft tissue image 47. In this embodiment, the calculations are carried out with the formula $$S2' = \left\{ \left(1 + \frac{\mu_L^T}{\mu_H^T}\right) S2 + \left(1 + \frac{\mu_L^B}{\mu_H^B}\right) SN \right\} \bigg/ 2 \cdot \left(\frac{\mu_L^B}{\mu_H^B} - \frac{\mu_L^T}{\mu_H^T}\right) \qquad (8)$$

Therefore, the noise components can be reduced even further.

As described above, the subtraction process described above in conjunction with FIG. 2 is substantially identical with that described above in conjunction with FIG. 6. The reason for this will be described hereinbelow.

The soft tissue image signal S2 expressed as Formula (2) and the noise signal SN expressed as Formula (7) are substituted into Formula (8). The bias component, such as C′ in Formula (2), is used to adjust the image density of the whole image which is obtained ultimately (and to adjust the luminance in cases where the image is displayed on a CRT display device, or the like). Therefore, in the operations described below, the bias component is not taken into consideration.

Substitution of Formulas (3) and (8) into Formula (9) yields $$S2' = \left\{ \left(1 + \frac{\mu_L^T}{\mu_H^T}\right)\left(\frac{\mu_L^B}{\mu_H^B} SO_2 - SO_1\right) + \left(1 + \frac{\mu_L^B}{\mu_H^B}\right)(S1 - \overline{S1}) \right\} \bigg/ 2 \cdot \left(\frac{\mu_L^B}{\mu_H^B} - \frac{\mu_L^T}{\mu_H^T}\right) \qquad (9)$$

Substitution of the bone image signal S1 expressed as Formula (1) into Formula (9) (with the bias component being ignored) yields $$S2' = \left\{ \left(1 + \frac{\mu_L^T}{\mu_H^T}\right)\left(\frac{\mu_L^B}{\mu_H^B} SO_2 - SO_1\right) + \left(1 + \frac{\mu_L^B}{\mu_H^B}\right)\left(SO_1 - \frac{\mu_L^T}{\mu_H^T} SO_2 - \overline{S1}\right) \right\} \bigg/ 2 \cdot \left(\frac{\mu_L^B}{\mu_H^B} - \frac{\mu_L^T}{\mu_H^T}\right) \qquad (10)$$

Transforming and rearranging Formula (10) yield $$S2' = (SO_1 + SO_2)/2 - \frac{\left(1 + \frac{\mu_L^B}{\mu_H^B}\right)}{2 \cdot \left(\frac{\mu_L^B}{\mu_H^B} - \frac{\mu_L^T}{\mu_H^T}\right)} \overline{S1} \qquad (11)$$

Substituting Formula (3) into Formula (11) yields $$S2' = SO - \frac{\left(1 + \frac{\mu_L^B}{\mu_H^B}\right)}{2 \cdot \left(\frac{\mu_L^B}{\mu_H^B} - \frac{\mu_L^T}{\mu_H^T}\right)} \overline{S1} \qquad (12)$$

Figure 7:
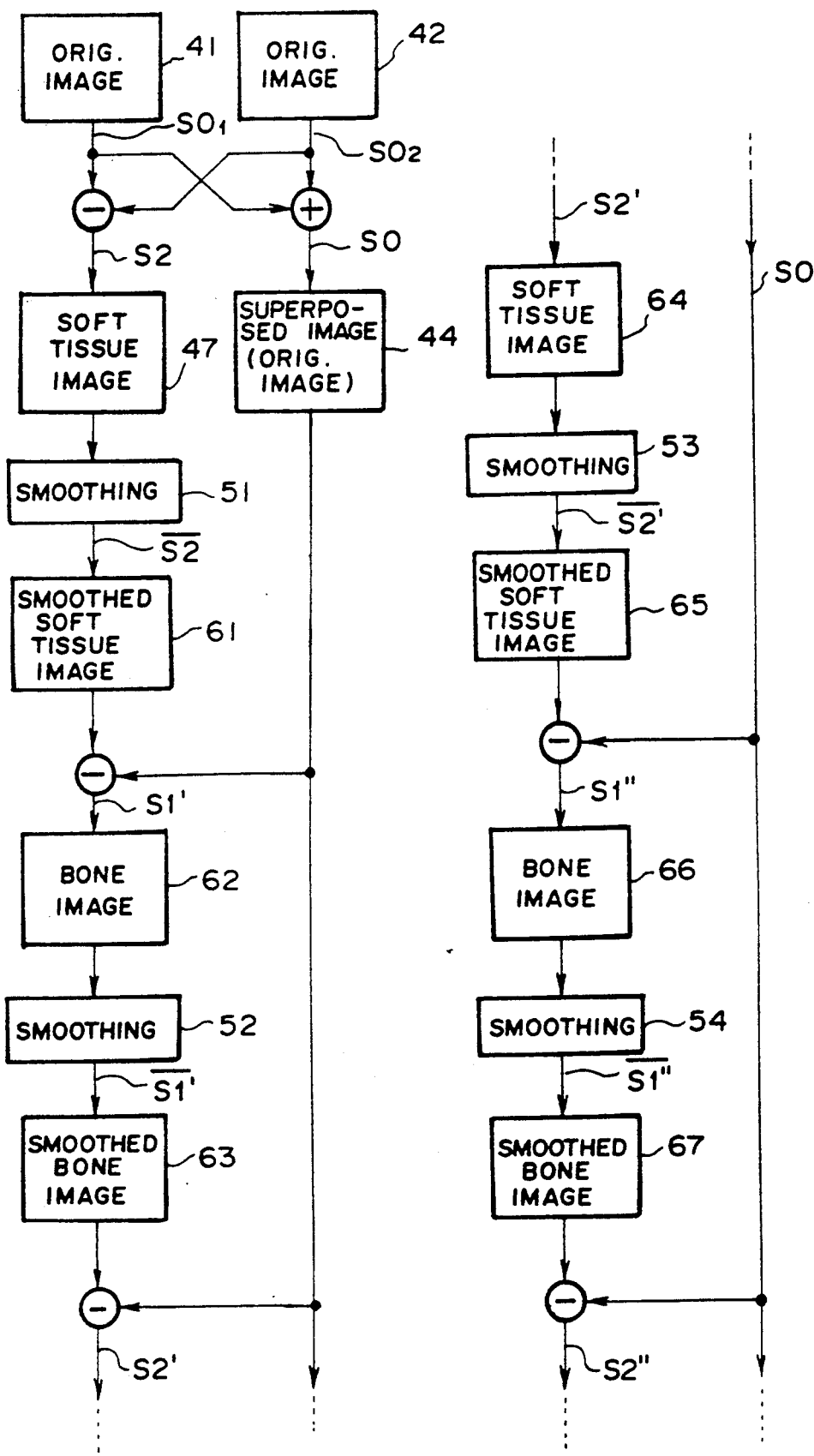
FIG. 7 is a flow chart showing the processes in accordance with another embodiment of the present invention.

Formula (12) is identical with Formula (6), except for the bias component. That is, the subtraction process described above in conjunction with FIG. 2 is substantially identical with that described above in conjunction with FIG. 6. FIG. 7 is a flow chart showing still another method for forming an energy subtraction image. FIGS. 8A through 8M are graphs showing the profiles of the images, which are shown in FIG. 7, along a predetermined direction.

In FIG. 7, similar elements are numbered with the same reference numerals with respect to FIG. 2 or FIG. 6.

FIGS. 8A and 8B show the profiles of the first X-ray image 41 and the second X-ray image 42, which are original images. Specifically, FIG. 8A shows how the values of the image signal components of the first image signal $SO_1$ representing the first X-ray image 41 are distributed, which image signal components represent the picture elements located along a predetermined direction (x direction) in the first X-ray image 41. FIG. 8B shows how the values of the image signal components of the second image signal $SO_2$ representing the second X-ray image 42 are distributed, which image signal components represent the picture elements located along the predetermined direction (x direction) in the second X-ray image 42. The levels of the first image signal $SO_1$ and the second image signal $SO_2$ are different from each other. However, each of the first image signal $SO_1$ and the second image signal $SO_2$ is composed of the image signal components, which represent the soft tissue patterns (corresponding to the hatched region in FIG. 8A or 8B) and have approximately uniform values, the image signal components, which represent the bone patterns and have values changing step-wise, and the random noise components. These three types of image signal components are superposed one upon another.

By carrying out the weighting subtraction process (indicated by the symbol ⊖ in FIG. 7) with Formula (2) on the first image signal $SO_1$ representing the first X-ray image 41 (original image) and the second image signal $SO_2$ representing the second X-ray image 42 (original image), the soft tissue image signal S2 representing the soft tissue image 47 is generated. Also, by carrying out the addition process (indicated by the symbol ⊖ in FIG. 7) with Formula (3) on the first image signal $SO_1$ and the second image signal $SO_2$, the superposition image signal SO representing the superposition image 44 is generated.

FIG. 8C shows how the values of the image signal components of the superposition image signal SO are distributed. Like the first image signal $SO_1$ shown in FIG. 8A and the second image signal $SO_2$ shown in FIG. 8B, the superposition image signal SO is composed of the image signal components, which represent the soft tissue patterns (corresponding to the hatched region in FIG. 8C) and have approximately uniform values, the image signal components, which represent the bone patterns and have values changing step-wise, and the random noise components. These three types of image signal components are superposed one upon another. However, the superposition image signal SO includes less noise components than the first image signal $SO_1$ shown in FIG. 8A and the second image signal $SO_2$ shown in FIG. 8B.

FIG. 8D shows how the values of the image signal components of the soft tissue image signal S2, which has been generated with Formula (2), are distributed. The soft tissue image signal S2 is primarily composed of the image signal components, which represent the soft tissue patterns and have approximately uniform values. However, the soft tissue image signal S2 includes more random noise components than the first image signal $SO_1$ shown in FIG. 8A and the second image signal $SO_2$ shown in FIG. 8B.

FIG. 8E shows how the values of the image signal components of the bone image signal S1, which may be generated with Formula (2), are distributed. (In this embodiment, the bone image signal S1 need not be generated.) The bone image signal S1 is primarily composed of the image signal components, which represent the bone patterns and have values changing step wise. However, like the soft tissue image signal S2 shown in FIG. 8D, the bone image signal S1 includes more random noise components than the first image signal $SO_1$ shown in FIG. 8A and the second image signal $SO_2$ shown in FIG. 8B.

As illustrated in FIG. 7, a smoothing process 51 is carried out on the soft tissue image signal S2, which represents the soft tissue image 47 and is distributed as shown in FIG. 8D. From the smoothing process 51, a smoothed soft tissue image signal $\overline{S2}$ is obtained, which represents a smoothed soft tissue image 61 and is distributed in the pattern shown in FIG. 8F. With the smoothing process 51, the spatial frequency components higher than a frequency of, for example, 1.0 cycle/mm are eliminated from the soft tissue image signal S2 representing the soft tissue image 47.

Thereafter, the superposition image signal SO and the smoothed soft tissue image signal $\overline{S2}$ are weighted, and the weighted smoothed soft tissue image signal $\overline{S2}$ is subtracted from the weighted superposition image signal SO. In this manner, a bone image signal S1' is obtained, which represents a bone image 62. As illustrated in FIG. 8G, the bone image signal S1' includes less random noise components than the bone image signal S1 shown in FIG. 8E. However, the bone image signal S1' slightly includes the high spatial frequency components of the soft tissue image 47 due to the smoothing process carried out on the soft tissue image 47.

A smoothing process 52 is then carried out on the bone image signal S1', which has been generated in the manner described above. With the smoothing process 52, patterns having low contrast and falling within the spatial frequency region higher than, for example, 0.5 cycle/mm are eliminated from the bone image 62 (i.e. small changes in the bone image signal S1' are eliminated). For this purpose, by way of example, the bone image signal S1' may be processed with a filter described below. Specifically, a window having an area corresponding to 0.5 cycle/mm is determined for a predetermined picture element P0. From the image signal components of the bone image signal S1' representing the picture elements belonging to the window, the image signal components are then found the values of which fall within the range of:

the value of an image signal component S1' representing the predetermined picture element P0 ± a predetermined value.

Thereafter, the mean value of the image signal components, which have thus been found, is calculated and employed as the value of a new image signal component $\overline{S1}'$ representing the predetermined picture element P0. With the smoothing process 52, a smoothed bone image signal $\overline{S1}'$ is obtained which represents a smoothed bone image 63. As illustrated in FIG. 8I, in the smoothed bone image signal $\overline{S1}$, the noise components have been reduced. Also, the high spatial frequency components of the soft tissue image 47 due to the smoothing process carried out on the soft tissue image 47 have been reduced. However, the rising part of the smoothed bone image signal $\overline{S1}'$ becomes unsharp.

Thereafter, the superposition image signal SO and the smoothed bone image signal $\overline{S1}$ are weighted, and weighted smoothed bone image signal $\overline{S1}$ is subtracted from the weighted superposition image signal SO. In this manner, a soft tissue image signal S2' is obtained which represents a soft tissue image 64. As illustrated in FIG. 8H, the soft tissue image signal S2' includes less noise components than the soft tissue image signal S2 shown in FIG. 8D. Also, because the rising part of the smoothed bone image signal S1' shown in FIG. 8I is unsharp, the information representing the corresponding part of the bone image is included as noise in the soft tissue image signal S2′. However, the level of random noise and the level of the information, which represents the bone image and constitutes noise, are very low. Therefore, a series of the processes may be finished in this step, and an unsharp mask process (to be described later) may be carried out on the soft tissue image signal S2′.

However, in this example, the same processes as those described above are repeated even further such that an image having better image quality may be obtained.

After the soft tissue image signal S2′ representing the soft tissue image 64 has been generated, a smoothing process 53 is carried out on the soft tissue image signal S2′. From the smoothing process 53, a smoothed soft tissue image signal $\overline{S2}$ is obtained, which represents a smoothed soft tissue image 65 and is distributed in the pattern shown in FIG. 8J. With the smoothing process 53, the spatial frequency components higher than a frequency of, for example, 1.5 cycle/mm are eliminated from the soft tissue image signal S2′.

Thereafter, the superposition image signal SO and the smoothed soft tissue image signal $\overline{S2}'$ are weighted, and the weighted smoothed soft tissue image signal $\overline{S2}'$ is subtracted from the weighted superposition image signal SO. In this manner, a bone image signal S1″ is obtained, which represents a bone image 66. As illustrated in FIG. 8K, the bone image signal S1″ includes less random noise components and less information, which represents the soft tissue image and constitutes noise, than the bone image signal S1′ shown in FIG. 8G. In cases where a bone image is to be reproduced, an unsharp mask signal may be obtained on the basis of the bone image signal S1″.

In this example, a smoothing process 54 is further carried out on the bone image signal S1″, which has been generated in the manner described above. From the smoothing process 54, a smoothed bone image signal $\overline{S1}''$ is obtained, which represents a smoothed bone image 67 and is distributed in the pattern shown in FIG. 8M. With the smoothing process 54, patterns having low contrast and falling within the spatial frequency region higher than, for example, 1.0 cycle/mm are eliminated from the bone image 66.

Thereafter, the superposition image signal SO and the smoothed bone image signal $\overline{S1}''$ are weighted, and weighted smoothed bone image signal $\overline{S1}''$ is subtracted from the weighted superposition image signal SO. In this manner, a soft tissue image signal S2″ is obtained. As illustrated in FIG. 8L, the soft tissue image signal S2″ includes less random noise components and less information, which represents the bone image and constitutes noise, than the soft tissue image signal S2′ shown in FIG. 8H.

In the manner described above, the smoothing processes and the weighting subtraction processes with respect to the superposition image signal SO (original image signal) are carried out repeatedly such that the bone images and soft tissue images, in which noise has been reduced sequentially, may be obtained alternately.

FIG. 9 is a flow chart showing still another method for forming an energy subtraction image which is substantially identical with the method described above in conjunction with FIG. 7 will be described hereinbelow. In FIG. 9, similar elements are numbered with the same reference numerals with respect to FIG. 7.

In the example of FIG. 9, the series of the processes for generating the bone image 62 in the example of FIG. 7 (which processes correspond to the processes described above with reference to FIG. 2, except that the bone image and the soft tissue image are interchanged with each other) are replaced by the processes described above with reference to FIG. 6. In the example of FIG. 9, the bone image and the soft tissue image in the processes shown in FIG. 6 are interchanged with each other. As described above, the example of FIG. 9 is substantially identical with the example of FIG. 7.

In the example of FIG. 9, only the initial processes in the embodiment of FIG. 7 are replaced by the processes described above with reference to FIG. 6. Such replacement may be carried out at an arbitrary stage of the processes carried out repeatedly. Such examples are substantially identical with the example of FIG. 7.

The processed soft tissue image signal S2′ which has been subjected to the subtraction process 70 (FIG. 1) and represents the processed soft tissue image 46 (The processed soft tissue image 46 obtained by the subtraction process shown in FIG. 2 is used to represent the processed soft tissue images obtained by the subtraction processes described above. The processed soft tissue image will be simply referred to as "the soft tissue image" and the processed soft tissue image signal S2′ will be simply referred to as "the soft tissue image signal", hereinbelow.) is subjected to the unsharp mask process 80. In this particular embodiment, the soft tissue image 46 and the soft tissue image signal S2′ are to be respectively interpreted as the extracted image and the extracted image signal described above.

Figure 10:
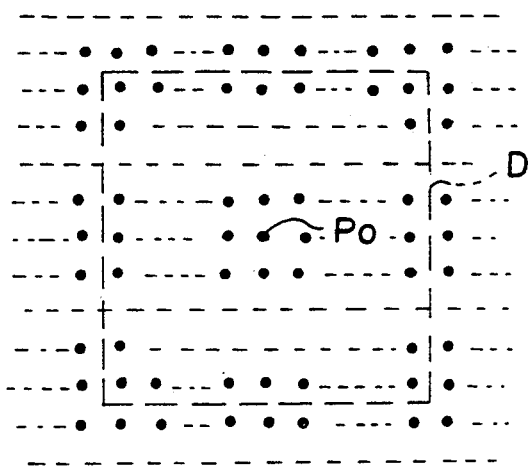
FIG. 10 is a view schematically showing numbers of picture elements which form the soft tissue image.

FIG. 10 schematically shows a number of picture elements forming the soft tissue image 46. Black dots in FIG. 10 respectively represents the picture elements and the soft tissue image signal S2′ has a value corresponding to each picture element.

When a predetermined picture element is represented by Po, the values of the soft tissue image signal S2′ corresponding to the picture elements in a predetermined region D having the predetermined picture element Po in its middle are averaged and the mean value thus obtained is employed as the unsharp mask signal Sus for the predetermined picture element Po. The operations are repeated for all the picture elements in the soft tissue image 46 sequentially taking each picture element as the predetermined picture element. Thus the unsharp mask signals Sus are obtained for all the picture elements in the soft tissue image 46 and an unsharp-mask-processed soft tissue image 81 is generated.

Figure 11:
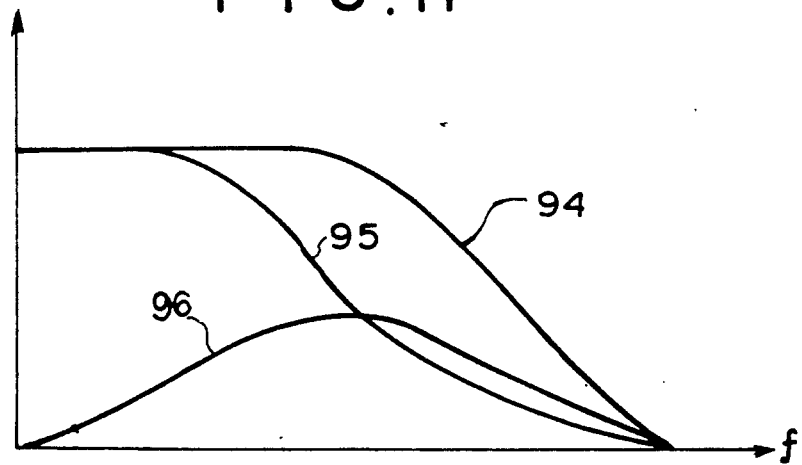
FIG. 11 is a graph showing spatial frequency spectra of a soft tissue image and an image obtained by processing the soft tissue image signal.

FIG. 11 is a graph showing spectra of the soft tissue image 46 and the image which is obtained by processing the soft tissue image signal S2′ with respect to the spatial frequency, f.

In FIG. 11, curve 94 indicates the spectrum of the bone image 43, and curve 95 indicates the spectrum of the unsharp-mask-processed soft tissue image 81. As can be seen from FIG. 11, the unsharp-mask-processed soft tissue image 81 has less high frequency components than the soft tissue image 46, and accordingly, in the unsharp-mask-processed soft tissue image 81, the low frequency components is relatively emphasized.

Thereafter, the unsharp mask signal Sus representing the unsharp-mask-processed soft tissue image 81 is subtracted from the soft tissue image signal S2′ representing the soft tissue image 46, whereby an image signal S3 representing a soft tissue emphasized image 82 wherein the high frequency components of the soft tissue image 46 is emphasized is generated. Thereafter the image signal S3 is multiplied by $\beta$ and then added to the original image signal SO1 representing the original image 41, whereby a processed image signal S' representing a processed image 83 is generated. The processed image signal S' is fed into the CRT display device 32 of the image processing and displaying apparatus 30 shown in FIG. 13, and a visible image is reproduced from the processed image signal S' and displayed on the CRT display device 32. Since the frequency response emphasizing process has been selectively applied to only the pattern of the soft tissues and the pattern of the bones has not been subjected to the frequency response emphasizing process, the pattern of the soft tissues in the visible image reproduced on the basis of the processed image signal S' has a good image quality and the pattern of the bones near the soft tissues is not so conspicuous.

Though several examples of the subtraction process for obtaining the soft tissue image 46 have been described above, the subtraction process need not be limited to those described above. However, it is preferred that a subtraction method which can sufficiently eliminate the noise components so that the noise components should not be emphasized by the frequency response emphasizing process. If the noise components are emphasized, the image quality is rather deteriorated.

Though, in the embodiment described above, the soft tissue emphasized image 82 is added to the original image 41 out of the two original images 41 and 42, it may be added instead to the original image 42 or to the superposition image 44 shown in FIG. 2 which is obtained by superposition of the original images 41 and 42. The present invention includes various modifications of the methods of calculation described above which are substantially equivalent to those described above. For example, since the present invention is based on the basic concept that the original image is equal to the soft tissue image plus the bone image, the soft tissue emphasized image 82 may be added to the bone image instead of the original image. Such equivalently modified methods of calculation are included in the scope of the present invention.

Though, in the aforesaid embodiments, the soft tissue image is subjected to the frequency response emphasizing process on the basis of X-ray images of the chest of a human body, the method is applicable widely when the pattern of one of a plurality of different tissues of a single object is mainly to be observed. For example, when the bone image is to be observed, the bone image may be obtained and subjected to the frequency response emphasizing process instead of the soft tissue image. Further, the frequency response emphasizing process may applied to an image in which the patterns of mammary glands have been emphasized, or an image in which the pattern of a malignant tumor has been emphasized.

Further, though, in the aforesaid embodiments, stimulable phosphor sheets are used, the method in accordance with the present invention is also applicable when other recording media, such as X-ray film (ordinarily combined with intensifying screens), are used.

What is claimed is:

1. A method of processing a radiation image comprising the steps of
    detecting a plurality of original image signals which represent a plurality of radiation images obtained by exposing recording media to radiations with different energy levels which have passed through an object constituted of a plurality of tissues exhibiting different levels of radiation absorptivity with respect to radiations with different energy levels,
    obtaining an extracted image signal representing an extracted image of a predetermined tissue in the object on the basis of said plurality of original image signals,
    obtaining a processed image signal representing a processed image by calculating a processed image signal component S' corresponding to a predetermined picture element in the extracted image according to formula $S' = S_{org} + \beta \cdot (S - S_{us})$ wherein Sus represents an unsharp mask signal obtained by averaging the extracted image signal components corresponding to a number of picture elements which surrounds a predetermined picture element within a predetermined region, Sorg represents the original image signal component corresponding to said predetermined picture element, S represents the extracted image signal corresponding to said predetermined picture element, and $\beta$ represents a coefficient, and by repeating the calculation according to said formula with all the picture elements in the extracted image being sequentially taken as said predetermined picture element, thereby obtaining processed image signal components for all the picture elements in the processed image.

2. A method of processing a radiation image as defined in claim 1 in which said extracted image signal is obtained by
    generating a second image signal, which represents a second image primarily composed of a pattern of a second tissue in said object other than said predetermined tissue, from the plurality of said original image signals,
    generating a smoothed image signal by processing said second image signal, said smoothed image signal representing a smoothed image in which noise components of said second image have been reduced or eliminated, and
    generating said extracted image signal by subtracting said smoothed image signal from an original image signal.

3. A method processing a radiation image as defined in claim 1 wherein a superposition image signal, which is obtained by carrying out an addition process on the plurality of said original image signals representing the plurality of said radiation images, is employed as said original image signal, from which said smoothed image signal is subtracted.

4. A method of processing a radiation image as defined in claim 1 in which said extracted image signal is obtained by
    carrying out a first process for generating a first image signal, which represents a first image primarily composed of patterns of first tissues of said object, from the plurality of said original image signals,
    thereafter carrying out a second process, which comprises the steps of generating a first smoothed image signal by processing said first image signal, said first smoothed image signal representing a first smoothed image in which noise components of said first image have been reduced, and generating a second image signal by subtracting said first smoothed image signal from an original image signal, said second image signal representing a second image primarily composed of patterns of second tissues of said object, and thereafter carrying out a third process, which comprises the steps of generating a second smoothed image signal by processing said second image signal, said second smoothed image signal representing a second smoothed image in which noise components of said second image have been reduced, and generating a new first image signal by subtracting said second smoothed image signal from an original image signal, said new first image signal representing a new first image primarily composed of the patterns of said first tissues of said object and corresponding to said extracted image signal representing said extracted image.

5. A method processing a radiation image as defined in claim 4 in which a superposition image signal, which is obtained by carrying out an addition process on the plurality of said original image signals representing the plurality of said radiation images, is employed as said original image signal, from which said first smoothed image signal is subtracted, and/or as said original image signal, from which said second smoothed image signal is subtracted.

6. A radiation image processing apparatus comprising
a subtraction processing means which detects a plurality of original image signals which represent a plurality of radiation images obtained by exposing recording media to radiations with different energy levels which have passed through an object constituted of a plurality of tissues exhibiting different levels of radiation absorptivity with respect to radiations with different energy levels, and obtains an extracted image signal representing an extracted image of a predetermined tissue in the object on the basis of said plurality of original image signals, and
a frequency response processing means which obtains a processed image signal representing a processed image by calculating a processed image signal component S' corresponding to a predetermined picture element in the extracted image according to formula $$S' = Sorg + \beta \cdot (S - Sus)$$

wherein Sus represents an unsharp mask signal obtained by averaging the extracted image signal components corresponding to a number of picture elements which surrounds a predetermined picture element within a predetermined region, Sorg represents the original image signal component corresponding to said predetermined picture element, S represents the extracted image signal corresponding to said predetermined picture element, and $\beta$ represents a coefficient, and by repeating the calculation according to said formula with all the picture elements in the extracted image being sequentially taken as said predetermined picture element, thereby obtaining processed image signal components for all the picture elements in the processed image.

7. An apparatus as defined in claim 6 in which said subtraction processing means obtains said extracted image signal by generating a second image signal, which represents a second image primarily composed of a pattern of a second tissue in said object other than said predetermined tissue, from the plurality of said original image signals, generating a smoothed image signal by processing said second image signal, said smoothed image signal representing a smoothed image in which noise components of said second image have been reduced or eliminated, and generating said extracted image signal by subtracting said smoothed image signal from an original image signal.

8. An apparatus as defined in claim 7 in which a superposition image signal, which is obtained by carrying out an addition process on the plurality of said original image signals representing the plurality of said radiation images, is employed as said original image signal, from which said smoothed image signal is subtracted.

9. An apparatus as defined in claim 6 in which said subtraction processing means obtains said extracted image signal by carrying out a first process for generating a first image signal, which represents a first image primarily composed of patterns of first tissues of said object, from the plurality of said original image signals, thereafter carrying out a second process, which comprises the steps of generating a first smoothed image signal by processing said first image signal, said first smoothed image signal representing a first smoothed image in which noise components of said first image have been reduced, and generating a second image signal by subtracting said first smoothed image signal from an original image signal, said second image signal representing a second image primarily composed of patterns of second tissues of said object, and thereafter carrying out a third process, which comprises the steps of generating a second smoothed image signal by processing said second image signal, said second smoothed image signal representing a second smoothed image in which noise components of said second image have been reduced, and generating a new first image signal by subtracting said second smoothed image signal from an original image signal, said new first image signal representing a new first image primarily composed of the patterns of said first tissues of said object and corresponding to said extracted image signal representing said extracted image.

10. An apparatus as defined in claim 9 in which a superposition image signal, which is obtained by carrying out an addition process on plurality of said original image signals representing the plurality of said radiation images, is employed as said original image signal, from which said first smoothed image signal is subtracted, and/or as said original image signal, from which said second smoothed image signal is subtracted.

* * * * *

UNITED STATES PATENT AND TRADEMARK OFFICE
CERTIFICATE OF CORRECTION

PATENT NO. : 5,291,403
DATED : March 1, 1994
INVENTOR(S) : Wataru ITO It is certified that error appears in the above-identified patent and that said Letters Patent is hereby corrected as shown below:

Cover page, item [30], change "Japan 2-82806 " to --Japan 2-282806--.

Signed and Sealed this

Ninth Day of August, 1994

Attest:

BRUCE LEHMAN

*Attesting Officer*  *Commissioner of Patents and Trademarks*